United States Patent [19]
Zaias et al.

[11] Patent Number: 5,647,866
[45] Date of Patent: Jul. 15, 1997

[54] METHOD OF HAIR DEPILATION

[76] Inventors: Nardo Zaias, 36 Star Island, Miami Beach, Fla. 33139; Thomas L. Mehl, Sr., 1015 Hwy. 337, Old Bronson Rd., Newberry, Fla. 32669

[21] Appl. No.: 645,868

[22] Filed: May 14, 1996

Related U.S. Application Data

[63] Continuation-in-part of Ser. No. 417,857, Apr. 7, 1995, abandoned, and Ser. No. 149,502, Nov. 9, 1993, abandoned.

[51] Int. Cl.$^6$ .............................. A61W 5/00; A61B 17/00
[52] U.S. Cl. .................................................................. 606/9
[58] Field of Search ............................... 606/3, 2, 14, 9, 606/13, 16, 17

[56] References Cited

U.S. PATENT DOCUMENTS

| | | | |
|---|---|---|---|
| 3,693,623 | 9/1972 | Harte et al. | 606/9 |
| 3,834,391 | 9/1974 | Block | 606/9 |
| 4,388,924 | 6/1983 | Weissman et al. | 606/9 |
| 4,617,926 | 10/1986 | Sutton | 606/9 |
| 5,059,192 | 10/1991 | Zaias . | |
| 5,226,907 | 7/1993 | Tankovich . | |
| 5,425,728 | 6/1995 | Tankovich . | |

FOREIGN PATENT DOCUMENTS

WO95/15725  6/1995  WIPO .

OTHER PUBLICATIONS

Treatment of Epidermal Pigmented Lesions With the Freqency-Doubled Q-Switched ND:YAG Laser Suzanne Linsmeier Kilmer, MD, Ronald G.Wheeland, MD David J. Goldberg, MD and R. Rox Anderson, MD. Dec. 1994, pp. 1515-1519.

Polyethylene-Glycol-mediated Delivery of Liposome-entrapped Pigments into Fibroblasts: Experimental Pigment Cells as Models for Mutator Phenotypes Stefan Schmitz, Theresa M. Allen and Kowichi Jimbow Dec. 1, 1992, pp. 6638-6641 and 6643-6645.

*Primary Examiner*—Lee S. Cohen
*Assistant Examiner*—Sonya Harris-Ogugua
*Attorney, Agent, or Firm*—Shlesinger Arkwright & Garvey

[57] ABSTRACT

The present invention relates to a method of hair depilation comprising the steps of providing an augmentation compound that readily absorbs a selected wavelength of laser light energy, encapsulating the augmentation compound within a liposimal carrier, applying an effective amount of the encapsulated augmentation compound to a region of tissue to be depilated sufficient to cause the compound to accumulate within the dermis surrounding each hair follicle and respective papilla, providing a laser light applicator capable of producing a wavelength of energy matched to the selected wavelength of absorption for the augmentation compound, positioning the laser light applicator above the region of skin treated with the augmentation compound and, applying a pulse of laser energy of the selected wavelength to the region of skin treated with the augmentation compound, the pulse of laser energy having a radiant exposure dose of sufficient energy and duration to cause damage to the hair follicle and papilla so that hair regrowth is prevented and surrounding tissue remains undamaged.

15 Claims, 4 Drawing Sheets

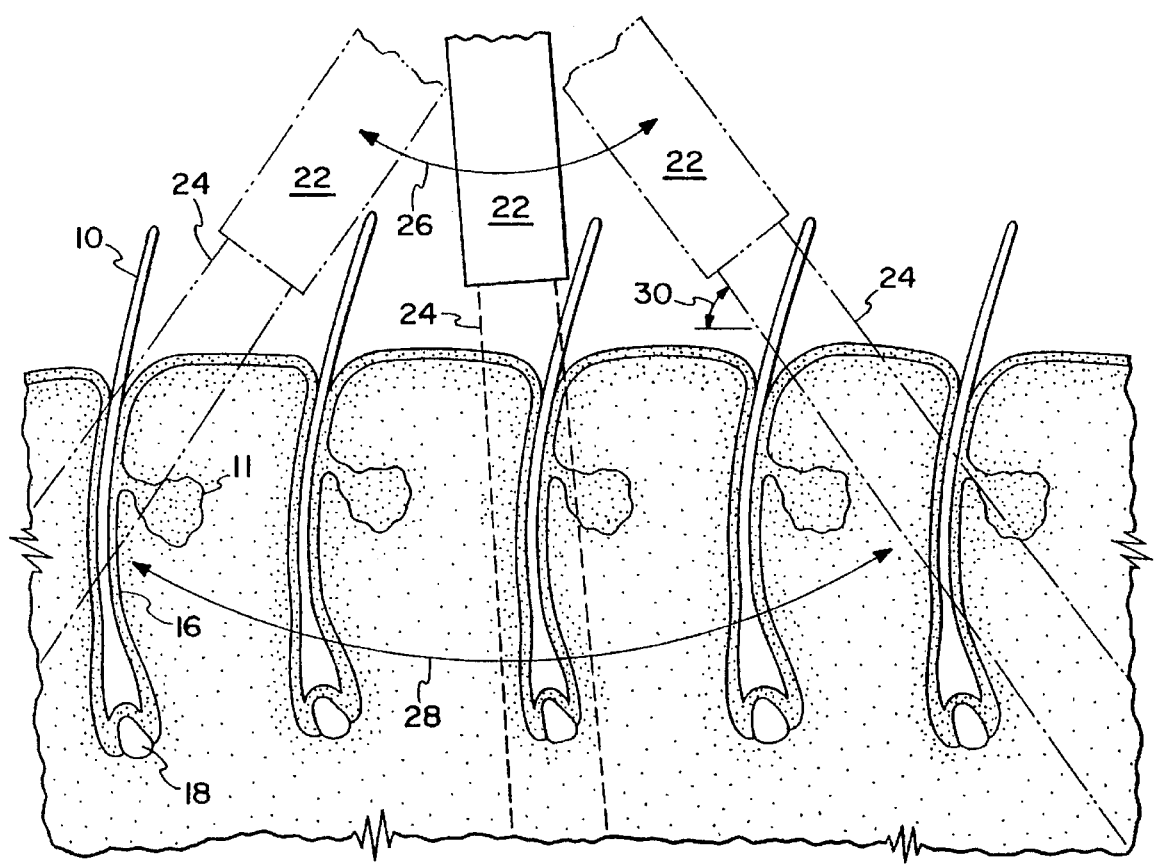
FIG. IC
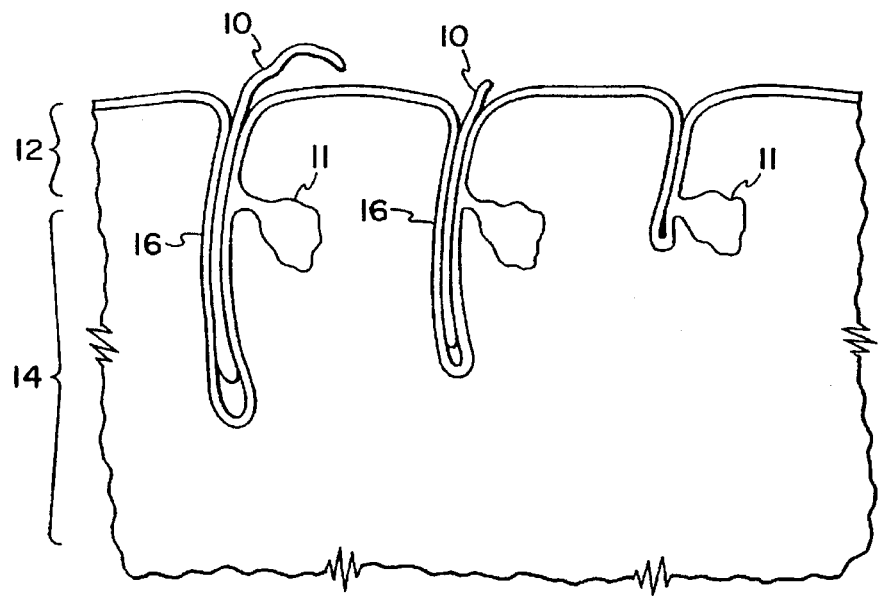
FIG. ID

METHOD OF HAIR DEPILATION

This application is a Continuation-In-Part of U.S. Ser. No. 08/417,857 filed Apr. 7, 1995 and U.S. Ser. No. 08/149,502, filed Nov. 9, 1993 both abandoned, each of which are incorporated herein by reference.

FIELD OF THE INVENTION

The present invention relates to a method of hair depilation involving treatment of the hair or group of hairs with a laser.

BACKGROUND OF THE INVENTION

Treatment of the skin with lasers has been the subject of study since the early 1960's. A variety of lasers have been used in dermatologic practice. Lasers are primarily distinguished by the wavelength of the light produced, measured in nanometers, such as the XeF excimer (351 nm), argon (488 nm, 514 nm), ruby (694 nm), Nd:YAG (1060 nm), and $CO_2$ (10,600 nm) lasers.

More recently, photothermolysis of skin has been demonstrated using xenon fluoride (XeF) laser and Q-switched ruby laser pulses. It has been discovered that radiation from Q-switched ruby lasers deeply penetrates the epidermis. This is accomplished, in part, by choosing a wavelength that is well absorbed by the specified target cells, with minimal absorption by adjacent tissues. One particular study entitled "Treatment of Epidermal Pigmented Lesions With the Frequency-Doubled Q-Switched Nd:YAG Laser", *Arch. Dermatology*, 130:1515–1519 (1994), teaches the removal of benign epidermal pigmented lesions through application of a frequency-doubled Q-switched Nd:YAG laser (532 nm). By selecting a laser capable of producing a wavelength strongly absorbed by melanin and controlling the pulse duration of the laser, the pigmented lesions are effectively targeted and the melanosomes destroyed.

It has been further discovered that the selective application of ruby red laser energy to hair will cause significant follicular damage to the extent that the hair will fall out. Applicants' previous U.S. Pat. No. 5,509,192, incorporated herein by reference, discloses a method whereby a ruby red laser is used to apply a pulse of laser energy to a single hair follicle, causing papilla damage and the resultant death of the follicle.

It has been proposed to apply specific types of contaminants to a section of the skin containing hair which is to be irradiated. The contaminant is selected on the basis of its ability to absorb a specific frequency band of light. U.S. Pat. Nos. 5,425,728 and 5,226,907 to Tankovich teach the application of a contaminant to the skin for purposes of infiltrating the hair duct itself. This prior art method does not teach or suggest the application of a contaminant to the surrounding structures of the hair i.e. the sebaceous gland, papilla or cappillaries, each of which are essential to hair growth and therefore permit regrowth following irradiation. The taught contaminants do not in and of themselves have the ability to be absorbed within these peripheral but essential structures of the hair. Because these regions are not treated with the contaminant, they remain unaffected following irradiation and regrowth of the hair will almost always occur.

In view of the above, a need has existed in the art for a more effective method of depiliation providing lasting results through application of a wavelenth absorbing contaminant/amplifier compound adapted to accumulate within the dermis surrounding each hair follicle and respective papilla.

OBJECTS AND SUMMARY OF THE INVENTION

It is an object of this invention to provide a method for depilation of hair and prevention of regrowth through the application of laser energy having a wavelength readily absorbed by hemoglobin.

Another object of the invention is to provide a method for treating a group of hairs simultaneously to depilate the same.

Still another object of the invention is to provide a method of laser-based hair removal that maximizes damage to those structures surrounding the hair follicle which are essential for nourishment and growth of the hair.

Yet another object of the present invention is to provide a method of hair removal that is readily administered to a large area of tissue by simply moving the laser during irradiation.

Yet another object of the present invention is to provide a method of hair removal including the application of laser energy to a hair follicle that has been pretreated with an amplifier or augmentation compound for purposes of enhancing the targeting of the laser to a specific region.

A further object is to provide an amplifier or augmentation compound that enables irradiation of the hair follicle and surrounding skin structure causing depiliation of the hair.

Another object is to provide an augmentation or amplifier compound adapted to enhance targeting of those surrounding structures of the hair known to be essential for hair growth. Destruction of those regions of the hair provides longer lasting depiliation.

In summary, the present invention relates to a method of hair depilation comprising the steps of providing an augmentation compound that readily absorbs a selected wavelength of laser light energy, encapsulating the augmentation compound within a liposimal carrier, applying an effective amount of the encapsulated augmentation compound to a region of tissue to be depilated sufficient to cause the compound to accumulate within the dermis surrounding each hair follicle and respective papilla, providing a laser light applicator capable of producing a wavelength of energy matched to the selected wavelength of absorption for the augmentation compound, positioning the laser light applicator above the region of skin treated with the augmentation compound and, applying a pulse of laser energy of the selected wavelength to the region of skin treated with the augmentation compound, the pulse of laser energy having a radiant exposure dose of sufficient energy and duration to cause damage to the hair follicle and papilla so that hair regrowth is prevented and surrounding tissue remains undamaged.

The present invention also relates to a method of hair depilation comprising the steps of providing a laser light applicator capable of producing a wavelength of energy matched to the absorption spectrum for hemoglobin, positioning the laser light applicator above a region of skin to be depilated, applying a pulse of laser energy having a wavelength that is readily absorbed by hemoglobin and having a radiant exposure dose of sufficient energy and duration to cause damage to the capillaries adjacent a hair papilla so that hair regrowth is prevented and the surrounding tissue remains undamaged.

Additional objects, advantages and features of the present invention will become apparent from a consideration of the following detailed description of the invention.

BRIEF DESCRIPTION OF THE DRAWINGS

FIG. 1C is a cross-sectional view of a region of tissue during irradiated with a laser after treatment with the augmentation compound;

FIG. 1D is a cross-sectional view of three hair shafts after irradiation according to the present invention and showing destruction of the hair follicle region;

DETAILED DESCRIPTION OF THE PREFERRED EMBODIMENT

Figure 1A:
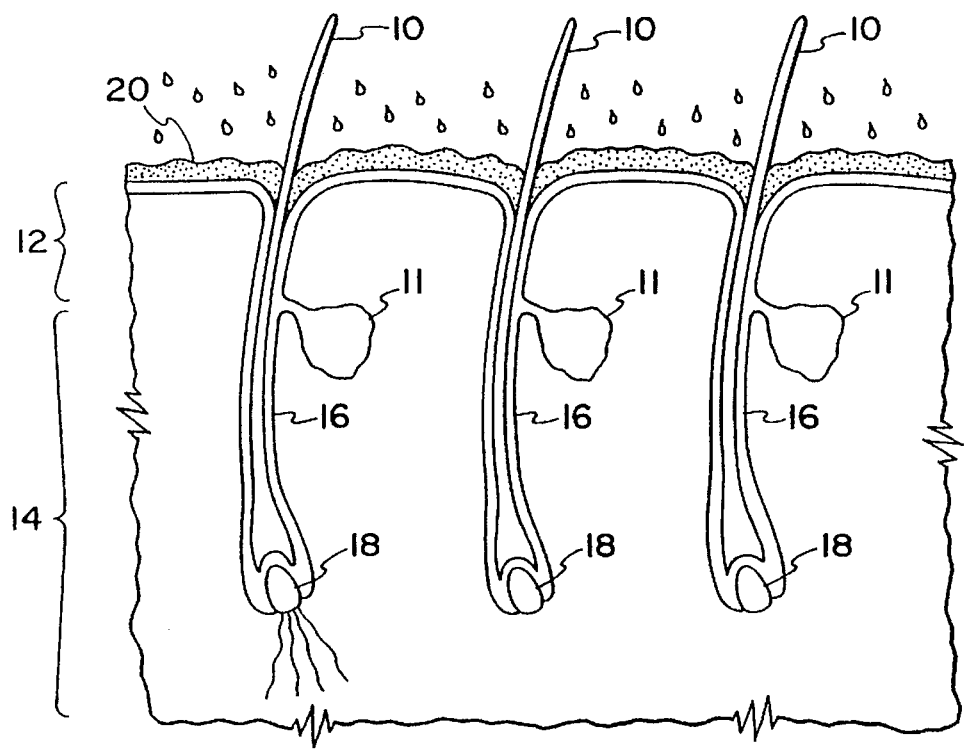
FIG. 1A is a cross-sectional view of three hair shafts receiving a coating containing augmentation compound prior to irradiation.

When applying a laser to living tissue, it is preferable to minimize the exposure required to achieve the objective sought. To this end, the following method of treatment has been developed in an effort to avoid unwanted side-effects, such a scarring or the inadvertent destruction of tissue unrelated to the targeted hair follicle matrix.

Using the process of selective photothermolysis, collateral tissue damage is minimized while at the same time heating and destruction of the hair follicle matrix is greatly improved. This is achieved by application of an augmentation or amplifier compound to the dermal region containing the hair, the augmentation compound being selected on the basis of its ability to readily absorb the specific wavelength of the laser thereby leaving the surrounding regions unaffected. Through application of the methods disclosed herein, the hair follicle is destroyed without permanently destroying adjacent dermal and epidermal structures.

In the present process, selective photothermolysis is employed whereby a laser is provided to generate a wavelength matched to the absorption spectrum of the selected enhancer or amplifier compound, preferably a melanin compound. For example, black melanin pigment or reddish-copper melanoid pigment, adapted to accumulate within the dermis surrounding each hair follicle and respective papilla, is first applied to the region of skin to be depiliated. Following absorbtion of the melanin through the dermis, the accumulated melanin is irradiated with a laser capable of producing a wavelength readily absorbed by the melanin pigments thereby selectively heating those regions of the hair matrix known to be essential to hair growth i.e. the cappillaries and papilla. Because the papilla includes a rich supply of small blood vessels and blood capillaries necessary for growth of the hair including the supply oxygen and nourishment thereto, the papilla are damaged by the heat generated from the pulsing laser causing degeneration of the follicle. There is no destruction of normal adjacent epidermal and dermal structures.

Representative lasers having wavelengths strongly absorbed by melanin within the black pigment absorption layer of the epidermis include the Q-switched ruby laser (694 nm), the short-pulsed red dye laser (504 and 510 nm), the copper vapor laser (511 nm) and the Q-switched neodymium (Nd):YAG laser having a wavelength of 564 nm that can be frequency doubled using a potassium diphosphate crystal to produce visible green light having a wavelength of 532 nm. The neodymium laser produces exceptionally strong melanin absorption at 532 nm and at a pulse duration of 10 nanoseconds and will sufficiently and effectively target the melanin enhancer compound deposited within the black pigment absorption layer of the epidermis.

The depth of penetration of the light coming from the laser is dependent upon its wavelength and therefore longer wavelengths are required to damage the region of the papilla located deeper within the dermis. Thus, the depth of penetration must also be determined through selection of the appropriate wavelength.

The laser selected may be provided to deliver the pulses of light energy through an aperture plate. The port in the aperture plate ranges in size from 3 mm up to 8 mm, preferably the port size of 8 mm when treating an entire areas of the body where multiple hairs are located.

The degree of follicular injury will be dependent upon the radiant exposure dose. Follicular damage is first observed at doses as low as 0.4 J/cm$^2$. At such a dose, the hair may fall out of the skin, however, normal regrowth may occur. Scaring has been found to occur at about 10 J/cm$^2$. Preferably, the applied dosage should fall within the range of about 0.4 J/cm$^2$ to about 10.0 J/cm$^2$ with a dose of about 8.0 J/cm$^2$ being optimum.

In accordance with the process of selective photothermolysis according to the present invention using lasers matched to a particular region in the epidermis to be irradiated, the pulse duration time period should be shorter than that of the thermal relaxation time for melanin. The thermal relaxation time is defined as the time it takes for a structure to cool to 50% of its peak temperature immediately following laser exposure. The calculated thermal relaxation time for melanosomes as been found to be approximately one microsecond. Therefore, selective damage those dermal regions containing the melanin-based augmentation or amplifier compound will occur when exposed to submicrosecond laser pulses. A Q-switch neodymium laser delivering pulses in the range of 30 to 40 nanoseconds has been found to adequately disrupt the melanin deposited within the hair follicle matrix.

Different types of melanin will require variations in the energy dose applied and the type of laser necessary to effect permanent hair removal. Generally speaking, darker melanin will induce more light scattering, therefore a high dosage may be required. However, treatment of all melanin-containing enhancer compounds used in accordance with the present invention can be effectively accomplished using a Q-switched neodymium laser through a potassium diphosphate crystal to produce a wave length of approximately 532 nm. The present invention further includes provision of an augmentation or enhancer compound containing melanin. Augmentation compounds according the present invention are adapted to be readily absorbed within the hair matrix and thus heighten the targeting ability of the laser. As noted above, the selected augmentation compound will have an absorption spectrum tailored to the wavelength generated by the laser. When applied to the dermis of the region to be depiliated, the compound is absorbed within the hair follicle matrix and upon irradiation, the laser energy will be concentrated in those critical areas of the hair matrix where the augmentation compound has collected i.e. hair shaft, papilla and sebaceous gland.

In an alternative embodiment of the present invention, a photosensitizer compound known to absorb a certain wavelength may be adapted for absorbtion within the hair follicle matrix. Following an initial irradiation with the laser, the absorbed compound becomes "activated" and a secondary compound is generated which readily absorbs a specified wavelength. For example, the photosensitizer compound could be of a type that activates and produces a red color which is readily absorbed by wavelengths of 600 to 700 nm. Consequently, regions of the skin not concentrated with the photosensitizer will not absorb the wavelengths produced by the laser and therefore not be damaged.

Delivery of the augmentation or enhancer compounds, preferably a melanin-based, to the hair follicle matrix can be achieved using microintradermal injection, liposomes encapsulation technology or ultrasonic technology, among other means for delivery of compounds into the dermal region of the skin.

In a preferred embodiment, liposomes are used to deliver the melanin-based augmentation compound to the hair matrix. Liposomes will provide site-specific transdermal delivery to the hair follicle matrix. In this embodiment, the melanin augmentation compound is microencapsulated within the liposome and topically applied to the epidermis of the skin. A non-toxic, dermatologically acceptable vehicle or carrier within which the liposome encapsulated augmentation compound is stable is preferred and will be evident to those of ordinary skill in the art. An emollient or lubricating vehicle that assists in hydrating the skin is especially preferred. An ointment base such as petrolatum, petrolatum plus volatile silicones and lanolin is also acceptable. Equally acceptable vehicles include cream bases which are mixtures of oils and water such as cold cream or hydrophilic ointments.

As noted above, the preferred carrier according to the present invention involves encapsulating the effective amount of melanin-based augmentation compound within a specific liposome to provide for efficient transdermal delivery of the compound through the layers of the skin. These liposomal augmentation compounds are topically applied to the skin and deliver the encapsulated melanin to the hair follicle region including papilla and sebaceous gland. The melanin is deposited virtually intact with little or no diffusion into tissue unassociated with the hair follicle matrix. Following delivery of the augmentation compound, irradiation with the laser results in highly specific targeting of the hair follicle matrix and destruction thereof.

Liposomes are microscopic spherical membrane-enclosed vesicles or sacks (20–30 mm in diameter) made artificially in the laboratory using a variety of methods. Within the scope of the present invention, the liposomes should be non-toxic to living cells and they should deliver the contents, in this case an augmentation compound into the follicle and immediately surrounding tissue with little or no diffusion during delivery. The liposomes according to the present invention may be of various sizes and may comprise either one or several membrane layers separating the internal and external compartments. An important element of the present invention is that a sufficient amount of augmentation compound be sequestered so that a relatively low concentration of augmentation compound is required for delivery to the hair follicle and further that the liposome be resistant to destruction as it travels from the surface of the skin where it is applied to the hair follicle. Liposome structures according to the present invention includes small unilamellar vesicles (less than 250 angstroms in diameter), large unilamellar vesicles (greater than 500 angstroms in diameter) and multilamellar vesicles depending upon the quantity of augmentation compound required to be encapsulated. In the present invention, small unilamellar vesicles are preferred since the augmentation compound according to the present invention is only required in low concentrations to absorb the desired wavelengths.

The liposomes according to the present invention may be made from natural and synthetic phospholipids, and glycolipids and other lipids and lipid congeners; cholesterol, cholesterol derivatives and other cholesterol congeners; charged species which impart a net charge to the membrane; reactive species which can react after liposome formation to link additional molecules to the lysome membrane; and other lipid soluble compounds which have chemical or biological activities.

The liposomes of the present invention may be prepared by combining a phospholipid component with an aqueous component containing the selected augmentation compound and under conditions which result in vesicle formation. The phospholipid concentration must be sufficient to form lamellar structures, and the aqueous component must be compatible with the augmentation compound selected. Methods for combining the phospholipid and the aqueous components so that vesicles will form include; drying the phospholipids onto glass and then dispersing them in the aqueous components; injecting phospholipids dissolved in a vaporizing or non-vaporizing organic solvent into the aqueous component which has previously been heated; and dissolving phospholipids in the aqueous base with detergents followed by removal of the detergents by dialysis. The lipoproteins can be produced from the foregoing mixtures either by sonication or by dispersing the mixture through either small bore tubing or through the small orifice of a French Press. The methods for producing liposomes as set forth in U.S. Pat. No. 5,077,211 to Yarosh are incorporated herein by reference.

It is in the scope of the present invention to use other methods for encapsulating the augmentation compound within a liposome. A specific example for producing the liposome follows. A lipid mixture as set forth above is dissolved in an organic solvent and dried to a thin film in a glass vessel. The selected augmentation compound is purified and added to the vessel at high concentrations in an aqueous buffer to rehydrate the lipid. The mixture is then agitated by vortexing and sonicated to form liposomes. The individual liposome spheres containing the encapsulated augmentation compound are then separated from the unincorporated augmentation compound by centrifugation or gel filtration. As noted earlier, the preferred augmentation or amplifier compound according to the present invention is liposomal encapsulated melanin. Melanin may be compartmentalized or entrapped within a liposome in accordance with the method taught in "Polyethylend-Glycol-mediated Delivery of Liposome-entrapped Pigments into Fibroblasts: Experimental Pigment Cells as Models for Mutator Phenotypes", *CANCER RESEARCH,* 52:6638–6645, (1992) the relevant portions of which are incorporated herein by reference.

The liposomal encapsulated melanin may be incorporated within a base material or other carrier noted above for administration to the skin. This administration to humans requires that the liposomes be pyrogen-free and sterile. To eliminate pyrogens, pyrogen-free raw materials, including all chemicals involved as well as the augmentation compound and water are used to form the liposomes. Sterilization can be performed by filtration of the liposomes through a 0.2 micron filter. A physiologically effective concentration of the liposomes may then be suspended in a buffered polymeric glycol gel carrier for even application to the skin. In general, the gel carrier should not include non-ionic detergents which can disrupt the liposome membranes.

Other similar vehicles can be used to topically administer the liposomes. The concentration of the enhancer or augmentation compound in the final preparation can vary over a wide range however within the scope of the present invention it is typically in the order of between about 0.0001% by weight to about 10% by weight of the carrier compound.

A general discussion of the liposomes and liposome technology can be found in an article entitled, "Liposomes" by Marc J. Ostro, published in *SCIENTIFIC AMERICAN*, January 1987, Vol. 256, pp. 102–111 and in a three volume work entitled, "Liposome Technology" edited by G. Gregorriadis, 1984, published by CRC Press, Boca Raton, Fla. the pertinent portions of which are incorporated herein by reference.

FIG. 1 illustrates multiple hair shafts 10 projecting below the epidermis region 12 of the skin and into the dermis 14 region. Each shaft 10 extends down the follicle 16 and includes a sebaceous gland 11 and which at the anagen stage of the hair cycle further includes a papilla 18. The papilla 18 is supplied with small blood vessels (not shown) that provide the growing hair with nourishment. The papilla 18 is an essential structure of the follicle matrix.

Figure 1B:
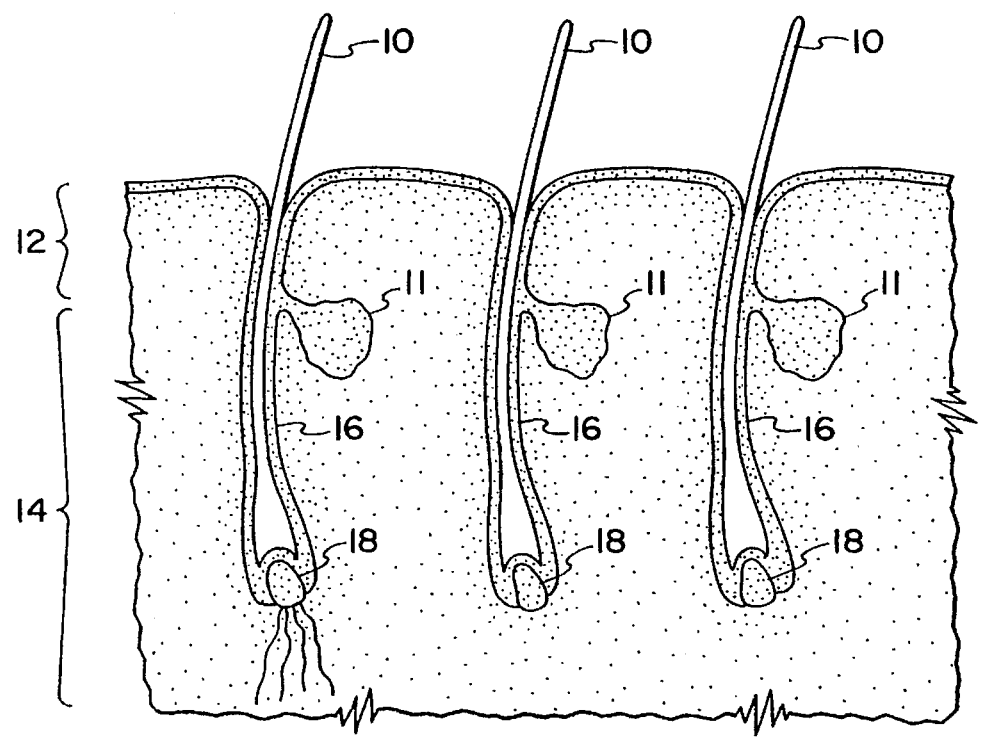
FIG. 1B is a cross-sectional view of the three hair shafts shown in FIG. 1A after absorption of the augmentation compound.

In order to assure sufficient entry and destruction of the papilla 18, use of a laser having sufficient energy and depth of penetration is required. FIG. 1A illustrates application of a coating 20 of the encapsulated augmentation compound to the epidermis 12. The augmentation compound, as noted earlier, may be a melanin that absorbs a particular wavelenth of light or other compound that, following irradiation, produces a color readily absorbable by a laser. FIG. 1B illustrates the absorption of the selected augmentation compound into the dermis 14 prior to irradiation and especially the localized dispersion of the compound around the hair matrix including shaft 16, papilla 18 and sebaceous gland 11.

As best shown in FIG. 1C the laser operator (not shown) will position a laser 22 substantially vertical over a hair follicle 16 such that an optimum location for aiming the laser pulse to strike the papilla 18 is obtained. The laser 22 is then moved about an arc from its vertical axis and in a direction shown by arrow 26 thereby moving the laser beam 24 along the surface of the skin and irradiating successive follicles 16 as shown by phantom lines and in the direction shown by arrow 28. In addition, the laser operator may change the positioning of the laser angle 30 for purposes of targeting a specific region of the hair follicle 16.

The angle 30 between the position of laser 22 and the surface of the skin 12 may likewise be varied between a generality perpendicular position relative to the surface of the skin to a substantially parallel position. It is therefore apparent that the laser operator may modify the angle of positioning of the laser in an effort to increase the area of irradiation thereby ensuring the entire tissue is irradiated appropriately. Because the augmentation or amplifier compound has accumulated within those critical regions of the hair matrix including follicle 16, papilla 18 and sebaceous gland 11, the laser can be swept across the skin or otherwise moved over a large area of skin to be treated without the prior art need for careful and absolute alignment over each hair to be depiliated.

Application of the laser pulse to the follicle 16 and the papilla 18 will cause photothermolysis and more particularly disruption of the hair follicle matrix including vaporization of the deposited melanin, capillary destruction to the papilla as well as vacuolation, edema, gas bubbles and protein denaturation. When the pulse applied to the hair follicle 16 is of sufficient level, these effects will seriously injure the hair follicle and papilla thereby damaging the hair germ which is responsible for hair regrowth.

Figure 2:
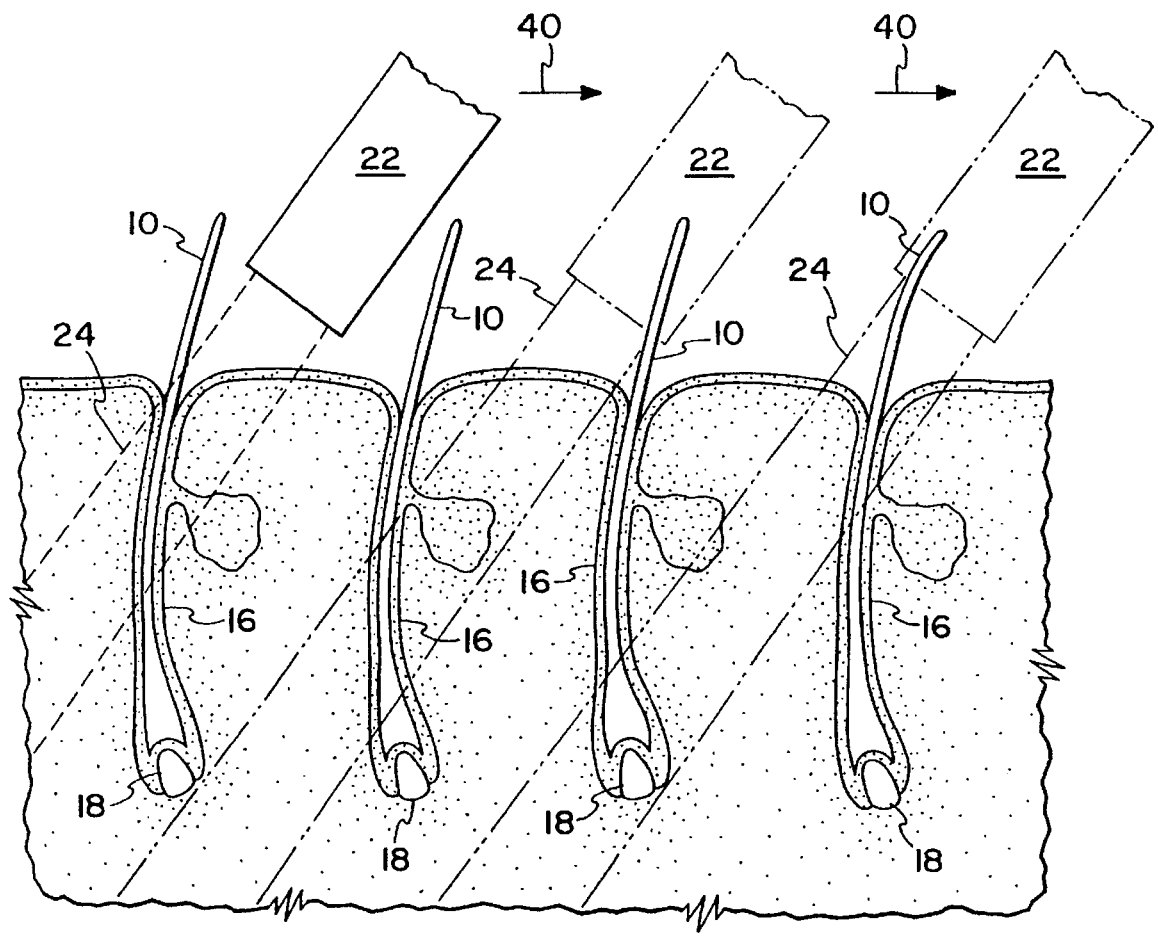
FIG. 2 is an alternative embodiment of laser irradiation.

FIG. 2 illustrates an alternative embodiment of the irradiation step shown in FIG. 1C. A laser 22 is shown positioned at an angle of about 60° to the skin surface. During irradiation, the laser 22 is moved lengthwise along the surface of the skin in the direction as shown by arrows 40 to irradiate the entire length of each hair follicle 16 including the respective papilla 18. Phantom lines illustrate the tracking of the beam 24 as it moves along each hair follicle shaft 16.

As best shown in FIG. 1D, the laser-damaged follicle 16 will gradually recede due to destruction of the matrix including disruption of blood flow from the capillaries to the papilla. The hair follicle 16 gradually atrophies without a blood supply thereby causing permanent hair removal.

Figure 3A:
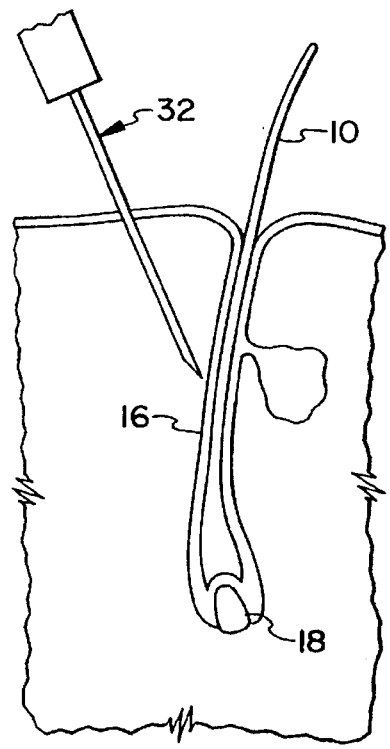
FIGS. 3A–3B is a cross-sectional view of a hair shaft whereby the augmentation compound is transdermally injected into the hair follicle region.
Figure 3B:
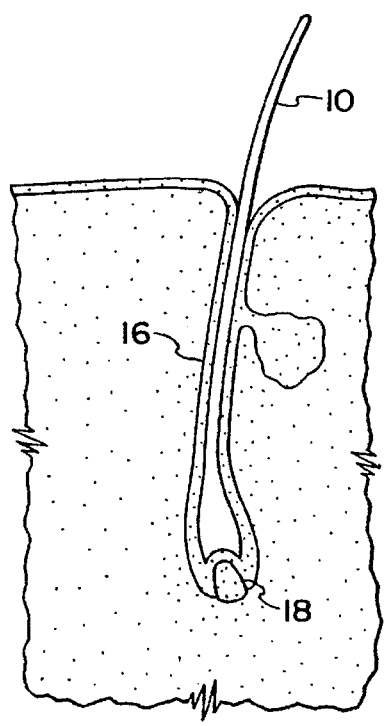
Figure 4A:
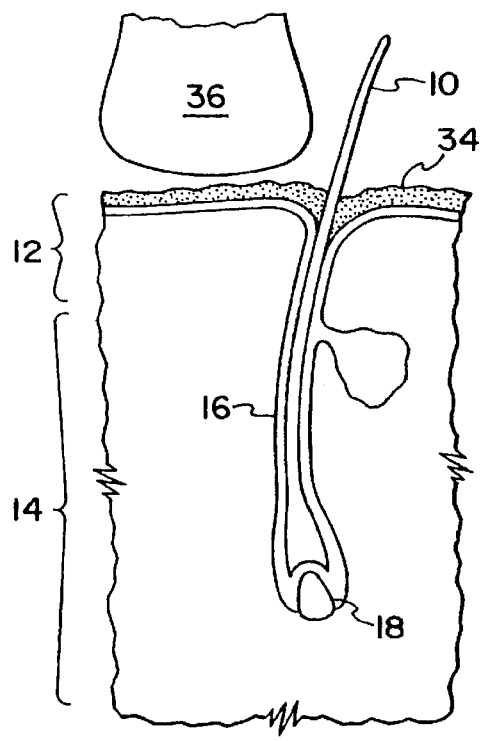
FIGS. 4A–4B is a cross-sectional view of a hair shaft whereby the augmentation compound is transdermally delivered to the hair follicle region through application of sonic energy.
Figure 4B:
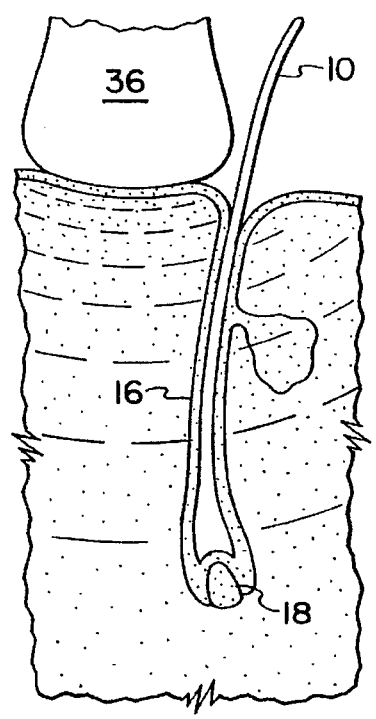

Turning to FIGS. 3A and 3B an alternative method for applying the augmentation compound is shown. A hypodermic needle 32 may be used for a transdermal injection of the augmentation compound resulting in dispersion of the augmentation compound around the hair follicle 16 as shown in FIG. 3B. Similarly, and as best shown in FIGS. 4A and 4B, a coating 34 containing the augmentation compound may be subjected to sonic energy applied by an applicator 36 which disperses the augmentation compound through the dermis and into the region surrounding the hair follicle 16. This embodiment may be used in conjunction with liposomes to assist in transdermal delivery of the augmentation compound.

Different types of hair and skin type will require different methods of delivery of the augmentation compound. In addition, certain augmentation compounds may be more readily delivered than others using a particular method of delivery. However, treatment of all varieties of hair are now possible without damage to the surround tissue through the use of an augmentation compound specifically tailored for use to absorb a specific wavelength from the laser. As noted earlier, through manipulation of the aperture plate size, the radiant exposure dose and thermorelaxation time can be made to adapt the method to any particular hair and skin type.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

I claim:

1. A method of hair depilation, comprising the steps of:
   a) providing an augmentation compound that readily absorbs a selected wavelength of laser light energy;
   b) encapsulating the augmentation compound within a liposimal carrier;
   c) applying an effective amount of the encapsulated augmentation compound to a region of tissue to be depilated suffficient to cause the compound to accumulate within the dermis surrounding each hair follicle and respective papilla:
   d) providing a laser light applicator capable of producing a wavelength of energy matched to the selected wavelength of absorption for the augmentation compound;

e) positioning the laser light applicator above the region of skin treated with the augmentation compound; and f) applying a pulse of laser energy of the selected wavelength with the laser light applicator to the region of skin treated with the augmentation compound, the pulse of laser energy having a radiant exposure dose of sufficient energy and duration to cause damage to the hair follicle and papilla so that hair regrowth is prevented and surrounding tissue remains undamaged.

2. The method of hair depiliation as set forth in claim 1, wherein:

a) the encapsulated augmentation compound is melanin.

3. The method of hair depiliation as set forth in claim 1, wherein:

a) applying the pulse of energy with the laser light applicator through an aperture having diameter of at least three millimeters.

4. The method of hair depiliation as set forth in claim 1, wherein:

a) the applied pulse of laser energy has an exposure dose between about 0.4 J/cm$^2$ and 10 J/cm$^2$ for a duration of less than about one microsecond.

5. The method of depiliation as set forth in claim 1, wherein:

a) the laser light applicator is a Q-switched ruby laser.

6. The method of depiliation as set forth in claim 1, wherein:

a) providing a radiant exposure dose is in the range of from about thirty to about forty nanoseconds.

7. The method of hair depiliation as set forth in claim 1, wherein:

a) the wavelength of the laser light applicator is closely matched to the absorbtion spectum of melanin.

8. The method of hair depiliation as set forth in claim 1, wherein:

a) applying the effective amount of encapsulated augmentation compound with a transdermal liposomal coating containing the augmentation compound.

9. The method of hair depiliation as set forth in claim 1, wherein:

a) applying the effective amount of encapsulated augmentation compound through application of a transdermal liposomal coating to the skin followed by application of sonic energy.

10. The method of hair depiliation as set forth in claim 1, wherein:

a) applying the effective amount of encapsulated augmentation compound with transdermal injection.

11. The method of hair depiliation as set forth in claim 1, and further including the step of:

a) moving the laser light applicator while applying the pulse of laser energy to the region of the skin.

12. The method of hair depiliation as set forth in claim 11, wherein:

a) the laser light applicator is moved laterally during application of the pulse of laser energy.

13. The method of hair depiliation as set forth in claim 1, wherein:

a) the laser light applicator is positioned substantially perpendicular to the surface of the skin to be treated.

14. The method of hair depiliation as set forth in claim 1, wherein:

a) the laser light applicator is positioned at an angle of about 60 degrees to the suface of the skin.

15. The method of hair depiliation as set forth in claim 11, wherein:

a) the laser light applicator is pivoted about a horizonatal axis during application of the pulse of laser energy.

* * * * *